US00PP19854P2

(12) United States Plant Patent
Glenn

(10) Patent No.: US PP19,854 P2
(45) Date of Patent: Mar. 24, 2009

(54) OAK TREE NAMED 'QSSTH'

(50) Latin Name: *Quercus shumardii*
Varietal Denomination: QSSTH

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 11/638,930

(22) Filed: Dec. 13, 2006

(51) Int. Cl.
*A01H 5/00* (2006.01)

(52) U.S. Cl. ..... Plt./225

(58) Field of Classification Search ..... Plt./225
See application file for complete search history.

(56) References Cited

U.S. PATENT DOCUMENTS

| | | | |
|---|---|---|---|
| PP4,149 | P | 11/1977 | Schmidt, III |
| PP13,524 | P3 | 1/2003 | Strickland |
| PP14,424 | P3 | 12/2003 | Strickland |
| PP16,254 | P3 | 2/2006 | Glenn |
| PP16,401 | P3 | 4/2006 | Glenn |

*Primary Examiner*—Annette H Para
(74) *Attorney, Agent, or Firm*—Klarquist Sparkman, LLP

(57) ABSTRACT

An Oak tree named 'QSSTH' having an upright branching habit and consistent red fall coloration, and also capable of being reproduced reliably using vegetative cuttings.

6 Drawing Sheets

Latin name of genus and species: *Quercus shumardii.*
Variety denomination: 'QSSTH'.

BACKGROUND OF THE INVENTION

The present invention relates to a new and distinct variety of *Quercus shumardii,* Shumard Oak, which has been given the varietal name 'QSSTH'.

The parentage of this tree is unclear. It is definitely a red oak type tree. Representative species include Pin Oak, Q. palustris, or Red Oak, Q. rubra, Nuttall Oak (Q. nuttallii), Shumard Oak (Q. shumardii), and Scarlet Oak (Q. coccinea). My new tree has characteristics that have prevented making an exact identification of its species, but Shumard Oak appears to be the closest.

Shumard Oak, as well as most other red oak types, readily hybridize with one another, and there is a high probability that this tree is a result of a cross between a Shumard Oak and Nuttall Oak or some other species of red oak, since Shumard Oak and Nuttall Oak overlap one another across much of their range. For example, in Texas, Shumard is located in a wide band covering most of the eastern part of the state, Nuttall is found in the lower Southeast corner of the state, and Texas Red Oak, Q. texana, is the primary tree in the central part of the state east of Dallas. There is also a large swath of habitat between the primary Shumard and Texas Red Oak regions where the predominant tree is a hybrid between Shumard and Texas Red Oak. Hybrids are common and can easily make up a large population of the trees in any given area.

My original tree had been purchased as a seedling tree growing in a one gallon container in fall 1996 and at that time was planted in a cultivated nursery field. In winter 2003, it was transplanted to an observation area where it has remained since that time. It is now 10 years old from a seed. The description of this new Oak variety is based on observations of this original tree and of asexually propagated progeny, asexually propagated in Oconee County, Ga., from vegetative propagation. These asexually propagated progeny are being grown at a nursery in Oconee County, Ga.

The original tree has displayed characteristics resembling Shumard Oak and Nuttall Oak. There is much confusion over the exact identification of this tree, and several experienced individuals have expressed differing opinions. The only consistency has been the opinion that the acorn is generally the most distinguishing characteristic determining the species difference between Shumard Oak and Nuttall Oak. When compared to the above oaks, the acorns on my new tree most resemble Shumard Oak, which indicates that the tree is most likely a Shumard Oak or at least has Shumard Oak as one of its parents. Other physical characteristics of the tree, such as leaf size, sinus depth, and bud features, do not provide definitive answers as to the true parentage of the tree.

BRIEF SUMMARY OF THE INVENTION

As I observed the original tree of my new variety, the uniqueness of this tree became apparent because of ascending branching properties, fast growth rate, and red fall color. These characteristics distinguish my new tree from other Shumard Oaks of which I am aware.

In 2002, progeny from my original tree were successfully propagated by vegetative cuttings at my direction, in Oconee Country, Ga., and the progeny have thus far proven to retain the upright branching habit and consistent red fall color of the original tree, even as smaller plants.

I observed this tree of my new variety for a period of time and believe it is particularly useful for groupings in lawns, parks, golf courses, commercial landscapes, and as a street tree. It provides good shade, has an above average growing rate, and has good upright structural branching. In addition, my new variety has consistent red fall color. This fall foliage color is absent from common Shumard Oak seedlings that generally have a fall foliage color of yellow-bronze to slight reddish coloration.

Cultivated Shumard Oak is represented in the industry mostly by seedling material. Seedling material has a wide range of variability, and, as is illustrated by information in this patent, there may be uncertainty as to the trueness of type from the seed. My new tree has an ascending branching habit and more vigorous growth rate not represented by any other Shumard Oak tree cultivar known to me. 'QSFTC' (U.S. Plant Pat. No. 14,424) is a Shumard Oak cultivar that has an upswept-pyramidal branching habit, and a consistent red fall colored foliage. However, this selection lacks the ascending branching habit and vigorous growth present on 'QSSTH'.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

My 'QSSTH' variety of Oak tree is currently growing at an observation site in Oconee County, Ga. It is located in an area of Oconee that has a clay loam soil type and receives approximately 50 inches of rain per year. Oconee County, Ga. is in USDA Hardiness Zone 7. Both Shumard and Nuttall are typically hardy in USDA Zones 5 through 9.

My new tree has not been observed under all growing conditions, and thus, variations may occur as a result of different growing conditions. The following is a detailed description of my new variety of my new tree with color terminology in accordance with The Royal Horticultural Society Colour Chart (R.H.S.) published by The Royal Horticultural Society in London. The observations are of the original tree growing and of asexually propagated progeny growing in Oconee County, Ga.

Parentage: Original tree purchased in a one gallon container and planted in a nursery field in Oconee County, Ga. The parentage of this tree is believed to include Shumard Oak, but is not extremely clear for reasons explained above.

Figure 1:
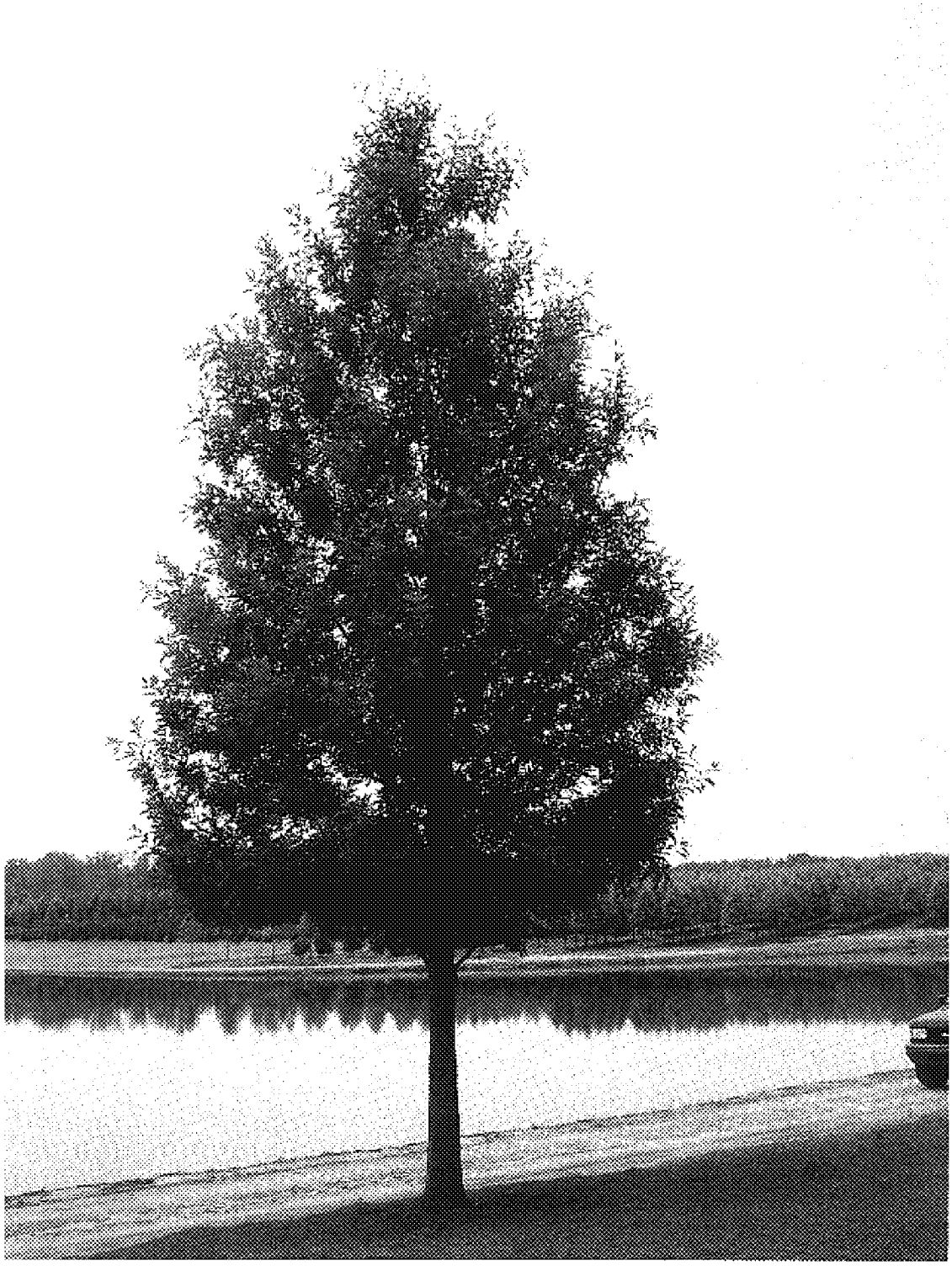
FIG. 1 is a photograph of the original tree of my new variety in summer leaf.
Figure 2:
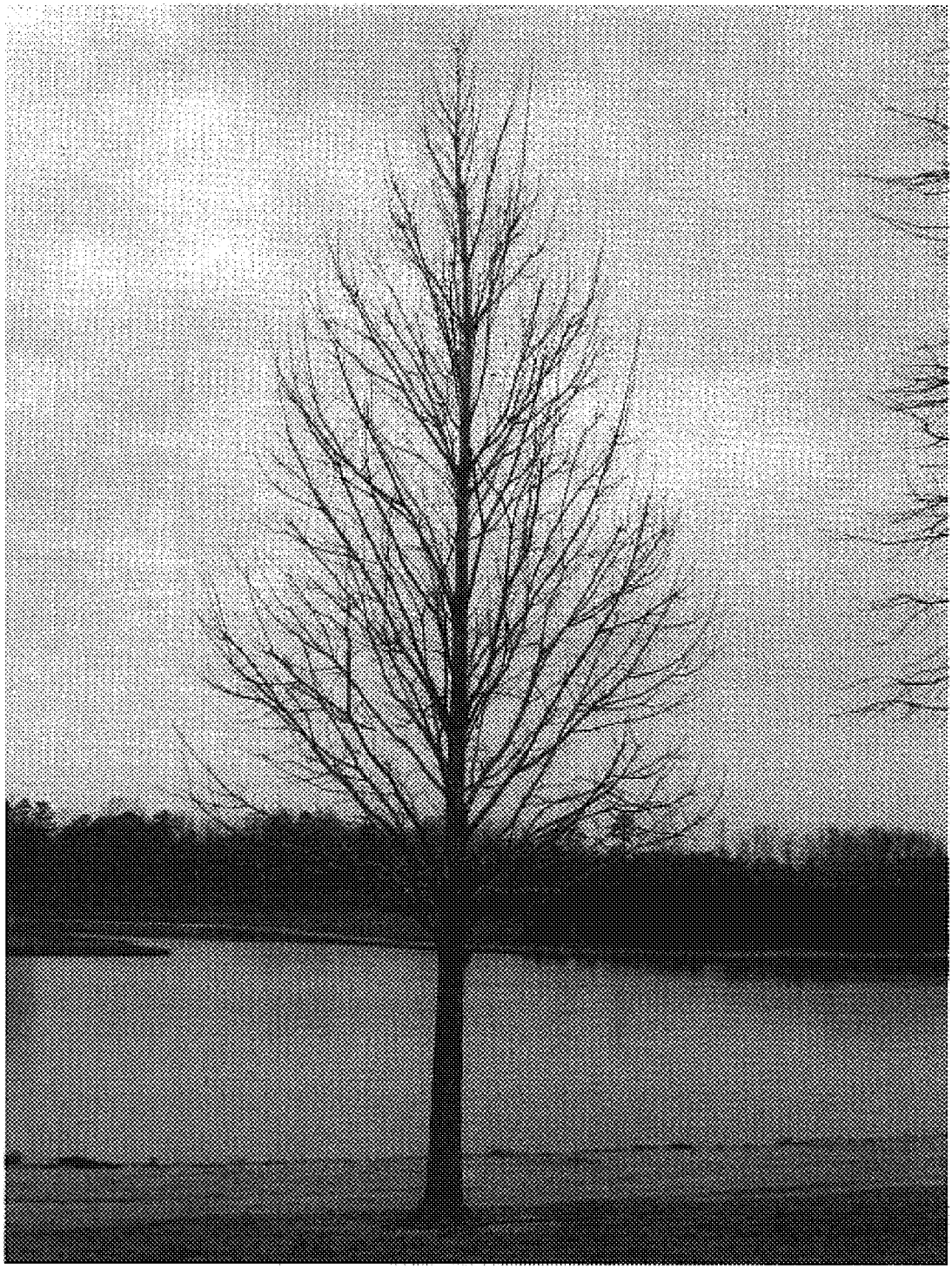
FIG. 2 is a photograph of the original tree of my new variety during the winter season.

Tree shape: The original tree has a dense canopy, is generally pyramidal, with a central leader (FIGS. 1 and 2).

Size and growth rate: The original tree is currently 10 inches in caliper at 12 inches above the ground, about 30 feet high, and about 14 feet wide, thus providing an overall height to width ration of about 2.14. Prior to transplanting to the observation site, the original tree had an average growth in caliper of about 0.94 inches per year. Root development from time of sticking cuttings is approximately six to eight weeks.

Trunk: Bark is typical of the species (FIG. 7), being smooth and gray (grayed-green) (RHS 197A) with patches of light gray (RHS 198D) on young trees, with age, becoming roughened by shallow ridges and furrows. Mature bark is similar to younger bark in color, also typical of the species.

Branching habit: Primary branches emerge from the trunk at about a 45 degree angle to the leader. Some of the branches in the top one-half of the tree emerge at slightly less of an angle, approximately a 35 degree angle to the leader. We expect with age the angle to increase with respect to the leader.

Figure 3:
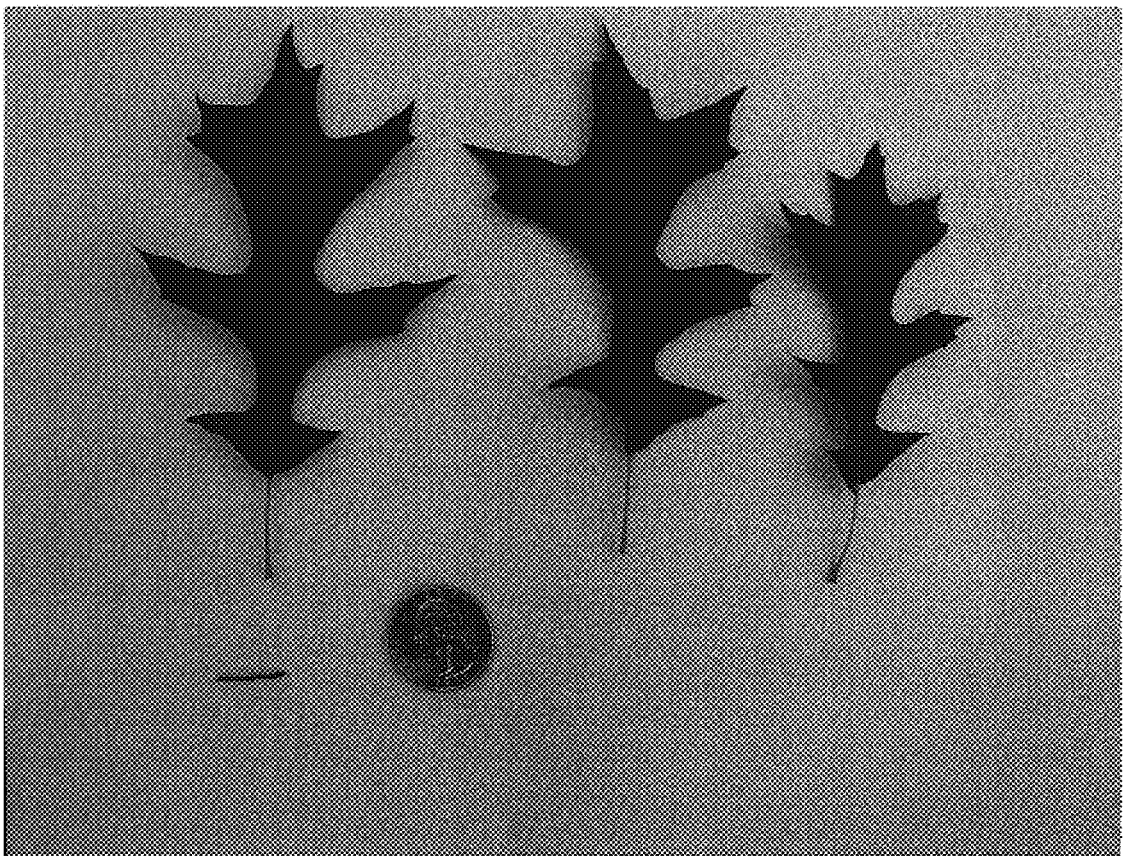
FIG. 3 is a close up of three single leaves depicting the upper side of leaves from a tree of my new variety. The US Quarter Dollar in the picture provides a sizing reference.
Figure 4:
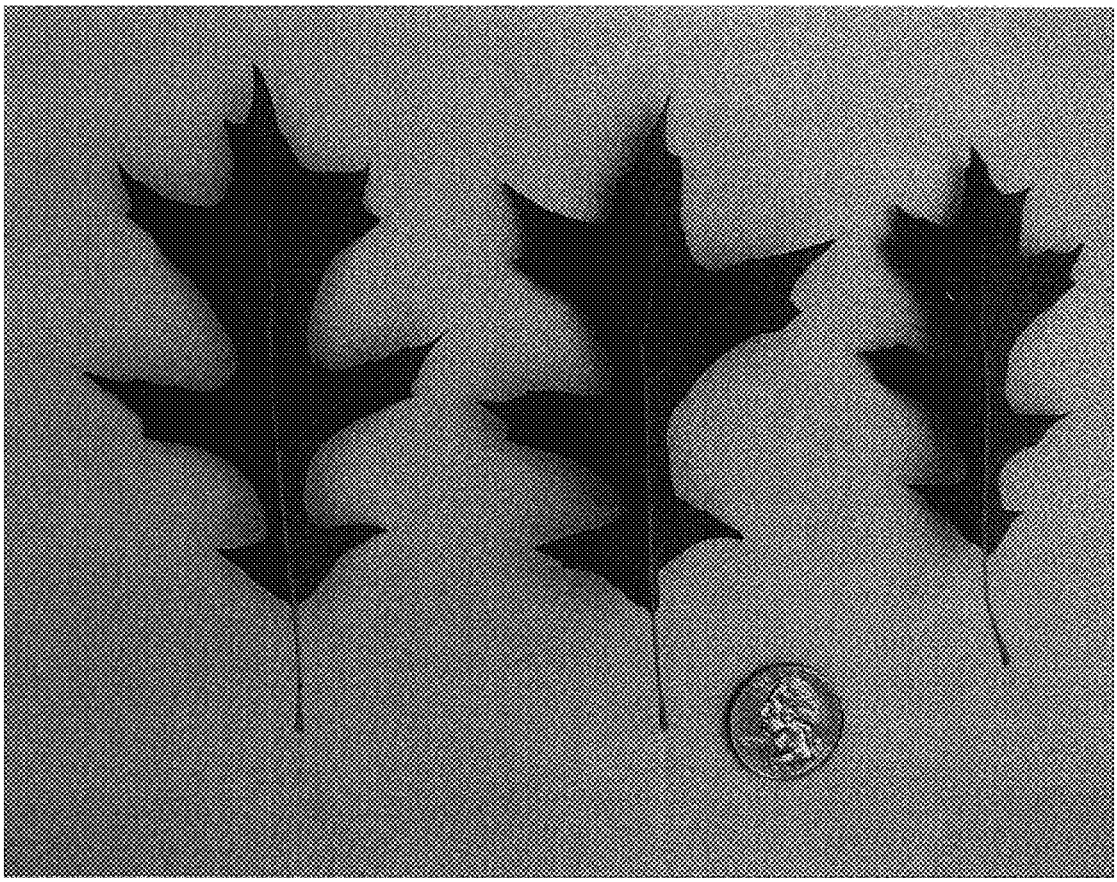
FIG. 4 is a close up of three single leaves depicting the under side of leaves from a tree of my new variety.
Figure 5:
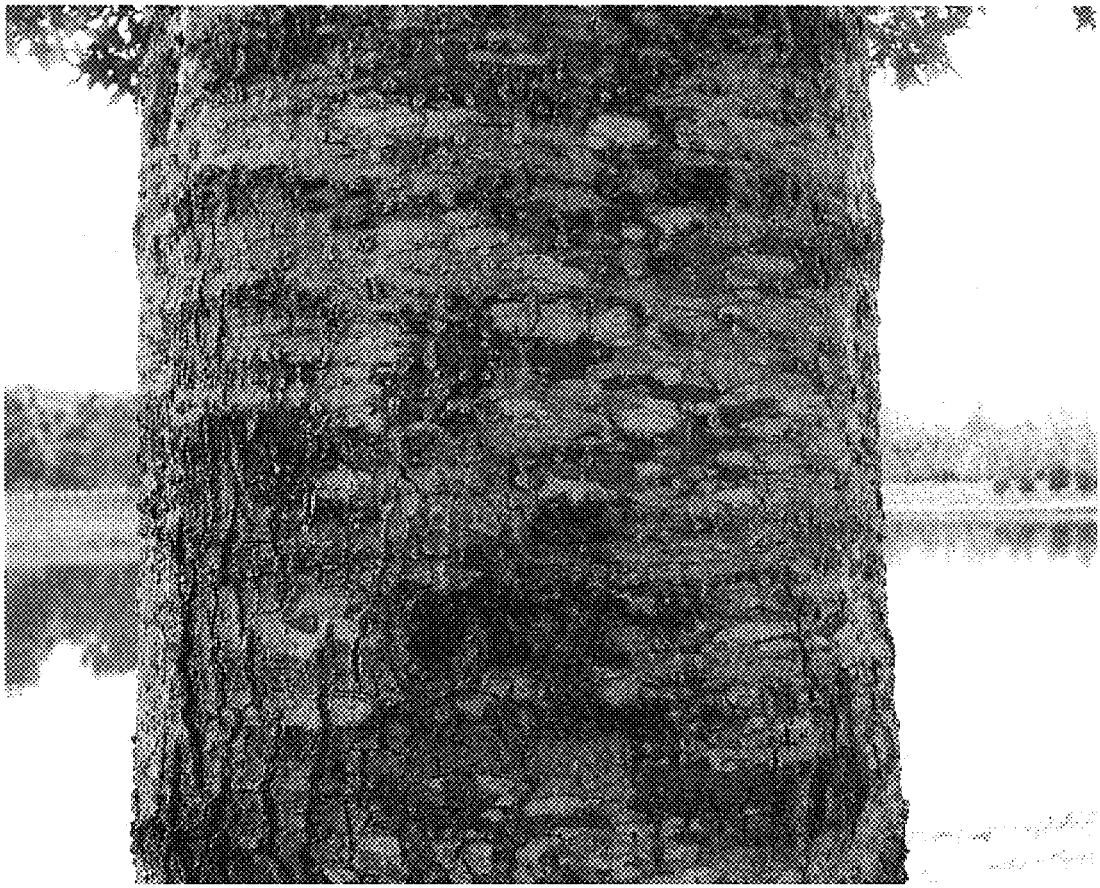
FIG. 5 is a close up of a typical section of the trunk of the original tree of the new variety.
Figure 6:
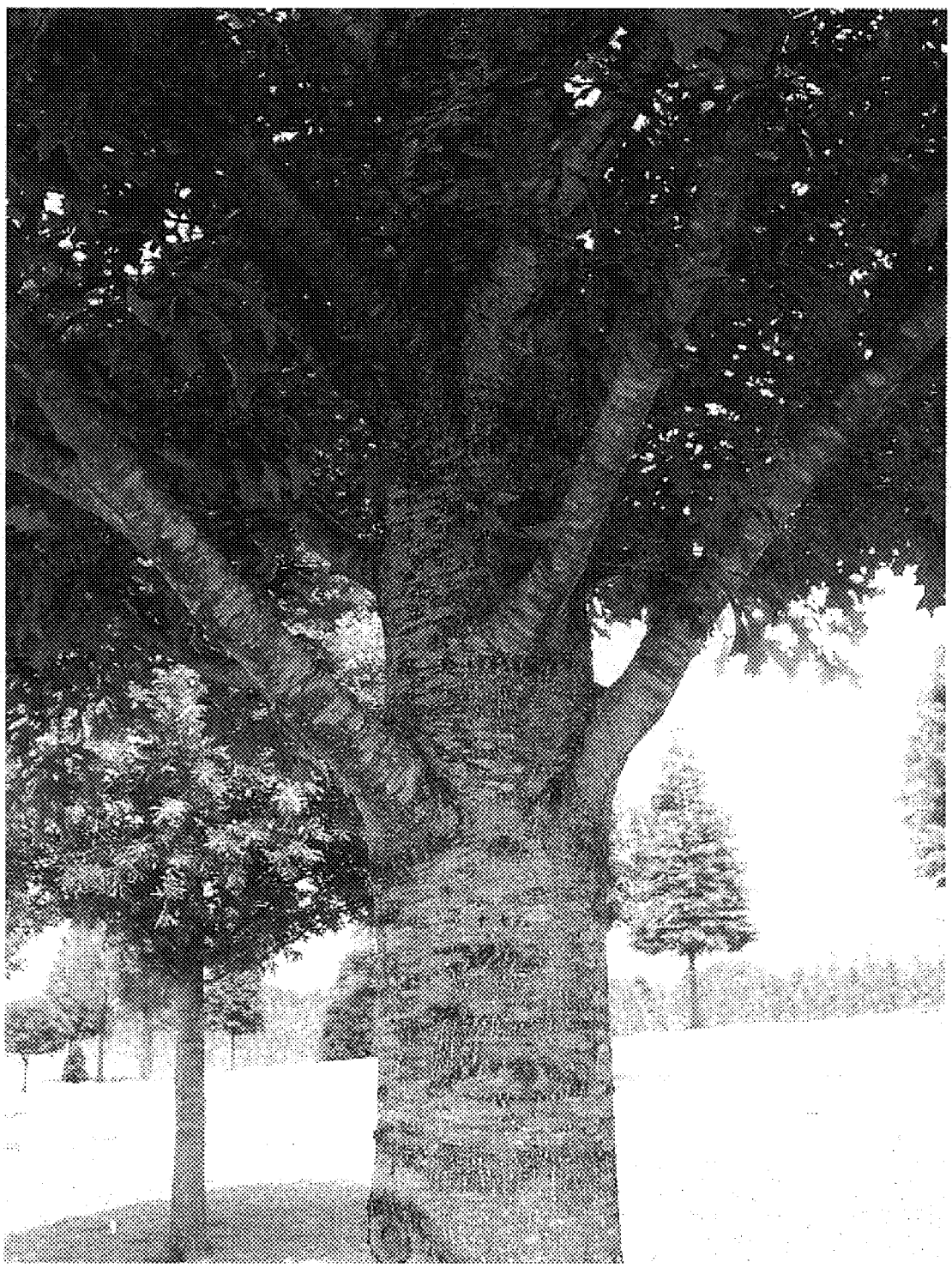
FIG. 6 is a close up of the branching habit of the new variety.

Foliage: The leaves of Shumard, Nuttall, and Pin all resemble one another, and my tree has leaves that are typical of the species Q. shumardii in size and shape: Alternate, simple, obovate to elliptic, 4 to 6" long, 3 to 4" wide, usually with 7 lobes, occasionally 9. Sinuses are often cut deeply almost to the midrib. The leaves maintain a lustrous dark green color in summer (FIG. 3) (RHS 139A), and the lower leaf surface (FIG. 4) is a lighter green (RHS 137B). My new tree has consistent red fall color.

Buds: Typical of the species, being imbricate, angle-ovoid, ¼ to ⅜" long, gray- or pale straw-colored, never reddish brown. Scales appear waxed.

Flowers: Typical of the species. However, most oaks have flowers so similar that it is difficult to distinguish between species based on flower type alone. The trees are monoecious. The staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual pistillate flowers consist of a 6-lobed calyx surrounding the ovary, with the whole partly enclosed in an involucre.

Fruit: Acorns are typical of species. Acorns are ovate, ¾ to 1" long, short-stalked, and covered only at the base by a hemispherical-shaped involucral cap. The acorn is striated with brown-black lines. The acorn is gray-orange in color with dark brown striations. The cap is light brown.

Root system: The root system is typical of the species, being fibrous.

Winter hardiness: Observed to be hardy in at least USDA Hardiness Zone 7. My new tree variety has not been observed under multiple Zones.

Disease and pest resistance: My new tree variety appears to be typical of the species.

I clam:

1. A new and distinct variety of Oak tree substantially as herein shown and described, characterized particularly as to novelty by its ascending branching habit, it vigorous growth habit and its consistent red fall coloration.

* * * * *

UNITED STATES PATENT AND TRADEMARK OFFICE

CERTIFICATE OF CORRECTION

PATENT NO. : PP 19,854 P2
APPLICATION NO. : 11/638930
DATED : March 24, 2009
INVENTOR(S) : Michael M. Glenn It is certified that error appears in the above-identified patent and that said Letters Patent is hereby corrected as shown below:

In the Specification:

Column 2, line 27, "Country" should read --County--

In the Claims:

Column 4, line 56, "it vigorous growth habit" should read --its vigorous growth habit--

Signed and Sealed this

Twentieth Day of April, 2010

David J. Kappos

David J. Kappos
*Director of the United States Patent and Trademark Office*